(12) United States Patent
Weber et al.

(10) Patent No.: US 7,778,684 B2
(45) Date of Patent: Aug. 17, 2010

(54) MRI RESONATOR SYSTEM WITH STENT IMPLANT

(75) Inventors: Jan Weber, Maple Grove, MN (US); Dave J. Sogard, Edina, MN (US); John Blix, Maple Grove, MN (US); David L. Friesen, Otsego, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 1267 days.

(21) Appl. No.: 11/198,961

(22) Filed: Aug. 8, 2005

(65) Prior Publication Data

US 2007/0032861 A1    Feb. 8, 2007

(51) Int. Cl.
*A61B 5/05* (2006.01)
*A61F 2/06* (2006.01)

(52) U.S. Cl. .............. 600/420; 600/424; 623/1.15; 623/1.16

(58) Field of Classification Search ......... 600/411, 600/420, 424, 1.44; 623/1.15, 1.16
See application file for complete search history.

(56) References Cited

U.S. PATENT DOCUMENTS

| | | |
|---|---|---|
| 4,768,507 A | 9/1988 | Fischell et al. |
| 4,963,313 A | 10/1990 | Noddin et al. |
| 4,985,233 A | 1/1991 | Klaveness et al. |
| 4,989,608 A | 2/1991 | Ratner |
| 5,154,179 A | 10/1992 | Ratner |
| 5,156,594 A | 10/1992 | Keith |
| 5,195,969 A | 3/1993 | Wang et al. |
| 5,270,086 A | 12/1993 | Hamlin |
| 5,352,431 A | 10/1994 | Hashiguchi et al. |
| 5,366,504 A | 11/1994 | Anderson et al. |
| 5,468,574 A | 11/1995 | Ehrenberg et al. |
| 5,593,419 A | 1/1997 | Segar |
| 5,674,242 A | 10/1997 | Phan et al. |
| 5,702,682 A | 12/1997 | Thompson |
| 5,714,110 A | 2/1998 | Wang et al. |
| 5,728,079 A | 3/1998 | Weber et al. |
| 5,744,958 A | 4/1998 | Werne |
| 5,817,017 A | 10/1998 | Young et al. |
| 5,840,387 A | 11/1998 | Berlowitz-Tarrant et al. |
| 5,895,385 A | 4/1999 | Guglielmi et al. |
| 5,944,714 A | 8/1999 | Guglielmi et al. |

(Continued)

FOREIGN PATENT DOCUMENTS

CA    2306769    *    4/2000

(Continued)

OTHER PUBLICATIONS

International Search Report received in PCT Application No. PCT/US2006/009818, mailed Jul. 5, 2006.

(Continued)

*Primary Examiner*—Eric F Winakur
*Assistant Examiner*—Katherine L Fernandez
(74) *Attorney, Agent, or Firm*—Vidas, Arrett & Steinkraus (57) ABSTRACT

A stent is adapted to be implanted into the lumen of a vessel. The stent includes struts and a resonating circuit tuned to the resonating frequency of a magnetic resonance imaging system. The resonant circuit is constructed of at least one inductor and at least one capacitor. The inductor is wound about at least one of the struts.

20 Claims, 6 Drawing Sheets

U.S. PATENT DOCUMENTS

| | | | |
|---|---|---|---|
| 6,123,920 A | 9/2000 | Gunther et al. | |
| 6,207,134 B1 | 3/2001 | Fahlvik et al. | |
| 6,249,076 B1 | 6/2001 | Madden et al. | |
| 6,280,385 B1 | 8/2001 | Melzer et al. | 600/423 |
| 6,423,296 B1 | 7/2002 | Gunther et al. | |
| 6,436,056 B1 | 8/2002 | Wang et al. | |
| 6,488,694 B1 | 12/2002 | Lau et al. | |
| 6,492,096 B1 | 12/2002 | Liu et al. | |
| 6,503,224 B1 | 1/2003 | Forman et al. | |
| 6,514,237 B1 | 2/2003 | Maseda | |
| 6,517,888 B1 | 2/2003 | Weber | |
| 6,595,952 B2 | 7/2003 | Forsberg | |
| 6,679,836 B2 | 1/2004 | Couvillon et al. | |
| 6,712,807 B2 | 3/2004 | Stivland et al. | |
| 6,749,556 B2 | 6/2004 | Banik | |
| 6,767,360 B1 * | 7/2004 | Alt et al. | 623/1.15 |
| 6,802,857 B1 | 10/2004 | Walsh et al. | 623/1.15 |
| 6,847,837 B1 | 1/2005 | Melzer et al. | 600/421 |
| 6,921,360 B2 | 7/2005 | Banik | |
| 6,942,682 B2 | 9/2005 | Vrba et al. | |
| 6,946,092 B1 | 9/2005 | Bertolino et al. | |
| 7,279,664 B2 * | 10/2007 | Weber | 219/635 |
| 2001/0056232 A1 | 12/2001 | Lardo et al. | |
| 2002/0013525 A1 | 1/2002 | Scott | |
| 2002/0022826 A1 | 2/2002 | Reynolds et al. | |
| 2003/0003220 A1 | 1/2003 | Zhong et al. | |
| 2003/0099684 A1 | 5/2003 | Domb | |
| 2003/0099764 A1 | 5/2003 | Li et al. | |
| 2003/0100830 A1 | 5/2003 | Zhong et al. | |
| 2003/0181972 A1 | 9/2003 | Jansen et al. | |
| 2003/0185895 A1 | 10/2003 | Lanphere et al. | |
| 2003/0212306 A1 | 11/2003 | Banik | |
| 2003/0236323 A1 | 12/2003 | Ratner et al. | |
| 2004/0024441 A1 | 2/2004 | Bertolino et al. | |
| 2004/0087982 A1 | 5/2004 | Eskuri | |
| 2004/0101564 A1 | 5/2004 | Rioux et al. | |
| 2004/0131808 A1 | 7/2004 | Schoenele et al. | |
| 2004/0143160 A1 | 7/2004 | Couvillon, Jr. | |
| 2004/0158310 A1 | 8/2004 | Weber et al. | |
| 2004/0181276 A1 | 9/2004 | Brown et al. | |
| 2004/0186377 A1 | 9/2004 | Zhong et al. | |
| 2004/0199239 A1 | 10/2004 | Austin et al. | |
| 2005/0002865 A1 | 1/2005 | Klaveness et al. | |
| 2005/0033407 A1 | 2/2005 | Weber et al. | 623/1.15 |
| 2005/0043712 A1 | 2/2005 | Devens, Jr. | |
| 2005/0070990 A1 | 3/2005 | Stinson | |
| 2005/0102017 A1 | 5/2005 | Mattison | |
| 2005/0107669 A1 | 5/2005 | Couvillon, Jr. | |
| 2005/0129727 A1 | 6/2005 | Weber et al. | |
| 2005/0165301 A1 | 7/2005 | Smith et al. | |
| 2005/0165439 A1 | 7/2005 | Weber et al. | |
| 2005/0192657 A1 | 9/2005 | Colen et al. | |
| 2005/0208100 A1 | 9/2005 | Weber et al. | |
| 2005/0261760 A1 | 11/2005 | Weber | |
| 2006/0265049 A1 * | 11/2006 | Gray et al. | 623/1.16 |

FOREIGN PATENT DOCUMENTS

| | | |
|---|---|---|
| CA | 2425813 | 4/2002 |
| WO | WO91/15152 | 10/1991 |
| WO | WO 99/19738 | 4/1999 |
| WO | WO 02/30331 | 4/2002 |
| WO | WO2005/013856 | 2/2005 |

OTHER PUBLICATIONS

Yi Liu et al., "All Polymer capacitor fabricated with inkjet printing technique," *Solid-Sate Electronics*, vol. 47 (2003) 1543-1548.

Hirad Samavati et al., "Fractal Capacitors," IEEE Journal of Solid State Circuits, vol. 33, No. 12 (Dec. 1998): 2035-2041.

David Needham et al., "The development and testing of a new temperature-sensitive drug delivery system for the treatment of solid tumors," *Advanced Drug Delivery Reviews*, vol. 53 (2001): 285-305.

Bunyarit Hemtanon et al; "Nanoparticle diode with Layer-by-layer deposition technique," $2^{nd}$ ECTI Annual Conference (ECTI-CON 2005), Pattaya, Thailand, May 12-13, 2005, 4pp.

A. Glidle et al., "XPS assaying of electrodeposited copolymer composition to optimize sensor materials," *Journal of Electron Spectroscopy and Related Phenomena*, vol. 121 (2001): 131-148.

Hua Huang et al., "Probe beam deflection study on electrochemically controlled release of 5-fluorouracil," *Electrochimica Acta*, vol. 43, No. 9 (1998): 999-1004.

Seung-Ki Lee et al., "Experimental Analysis on the Properties of Polypyrrole as Drug Delivery System Materials," *Smart Structures and Materials 2003*: Electroactive Polymer Actuators and Devices (EAPAD), ed. Yoseph Bar-Cohen, Proceedings of SPIE, vol. 5051 (2003): 338-348.

Ronald L. Blankespoor et al., "Polymerized 3-Methoxythiophene. A Processable Material for the Controlled Release on Anions," *J. Chem Soc., Chem. Commun.*, (1985): 90-92.

An-Cheng Chang et al., "Electrochemically Controlled Binding and Release of Salicylate, TCNQ and Ferrocyanide from Films of Oligomeric 3-Methoxythiophene," *J. Electroanal. Chem.*, vol. 247 (1988): 173-184.

Baruch Zinger et al., "Timed Release of Chemicals from Polypyrrole Films," *J. Am. Chem. Soc*, vol. 106 (1984): 6861-6863.

Benoit Piro et al., "Electrochemical method for entrapment of oligonucleotides in polymer-coated electrodes," J. Biomed. Mater. Res., vol. 46, No. 4 (1996).

Functionalization of Polymer Surfaces, Europlasma Technical Paper, May 8, 2004, 29pp.

D.G. Kurth et al., "Multilayers on Solid Planar Substrates: From Structure to Function," chap. 14, Multi-layer Thin Films, Sequentially Assembly of Nanocomposite Materials, Wiley-VCH, ISBN 3-527-30440-1, pp. 393-426.

Winky L.W. Hau et al., "Surface-chemistry technology for microfluidics," Journal of Micromechanics and Microengineering, vol. 13 (2003) 272-278.

Dan Li et al., "Fabrication of a prototype humidity-sensitive capacitor via layer-by-layer self-assembling technique," *Materials Science and Engineering*, C11(2000): 117-119.

Srivatsan Kidambi et al., "Selective Depositions on Polyelectrolyte Multilayers: Self-Assembled Monlayers of m-dPEG Acid as Molecular Template," *J. Am. Chem. Soc.*, vol. 126 (2004): 4697-4703.

Yanjing Liu et al., "Layer-by-Layer ionic self-assembly of Au colloids into multilayer thin-films with bulk metal conductivity," *Chemical Physics Letters*, vol. 298 (1998): 315-319.

Alexei A. Antipov et al., "Polyelectrolyte multilayer capsules as vehicles with tunable permeability," Advances in Colloid and Interface Science, vol. 111 (2004): 49-61.

Rana M. Jisr et al., "Hydrophobic and Ultrahydrophobic Multilayer Thin Films from Perfluorinated Polyelectrolytes," *Agnew. Chem. Int. Ed.*, vol. 44 (2005): 782-785.

E.E. Tzirtzilakis, "A mathematical model for blood flow in magnetic field," Physics of Fluids, vol. 17 (2005): 077103-15.

Elisabeth Smela et al., "Electrochemically Driven Polypyrrole Bilayers for Moving and Positioning Bulk Micromachined Silicon Plates," *Journal of Microelectrochemical Systems*, vol. 8, No. 4 (Dec. 1999): 373-383.

Thierry P. Cassagneau et al., "Electron Transfer and Charge Storage in Ultrathin Films Layer-by-Layer Self-Assembled from Polyelectrolytes, Nanoparticles and Nanoplatelets," *Electrochemistry of Nanomaterials*, ed Gary Hodes, May 2001.

Fa-Hsuan Lin et al., "Degenerate Mode Birdcage Volume Coil for Sensitivity-Encoded Imaging," *Magnetic Resonance in Medicine*, vol. 50 (2003): 1107-1111.

Straumal et al., "Vacuum Arc Deposition of Protective Layers on Glass and Polymer Substrates", *Thin Solid Films* 383: 224-226 (2001).

Zimmerman-Paul et al., "High Resolution Intravascular Magnetic Resonance Imaging: Monitoring of Plaque Formation in Heritable Hyperlipidemic Rabbits", *Circulation* 1054-1062 (Mar. 2, 1999).

Larmor Frequency calculator (1 page), Retrieved from the Internet on Jan. 6, 2006.

Blending Tradition and Technology 2003 http://www.geostevens.com (1 page).

Farhat et al., "Corrosion Control Using Polyelectrolyte Multilayers", *Electrochemical and Solid State Letters*, 5(4): B13-B15 (2002).

Schetsky et al., "Shape Memory Alloys", Encyclopedia of Chemical Technology ($3^{rd}$ Ed.)., John Wiley & Sons, 1982, vol. 20, pp. 726-736.

* cited by examiner

MRI RESONATOR SYSTEM WITH STENT IMPLANT

CROSS-REFERENCE TO RELATED APPLICATIONS

Not Applicable

BACKGROUND OF THE INVENTION

1. Field of the Invention

In some embodiments this invention relates to implantable medical devices, their manufacture, and methods of use. Some embodiments are directed to delivery systems, such as catheter systems of all types, which are utilized in the delivery of such devices.

2. Description of the Related Art

A stent is a medical device introduced to a body lumen and is well known in the art. Typically, a stent is implanted in a blood vessel at the site of a stenosis or aneurysm endoluminally, i.e. by so-called "minimally invasive techniques" in which the stent in a radially reduced configuration, optionally restrained in a radially compressed configuration by a sheath and/or catheter, is delivered by a stent delivery system or "introducer" to the site where it is required. The introducer may enter the body from an access location outside the body, such as through the patient's skin, or by a "cut down" technique in which the entry blood vessel is exposed by minor surgical means.

Stents, grafts, stent-grafts, vena cava filters, expandable frameworks, and similar implantable medical devices, collectively referred to hereinafter as stents, are radially expandable endoprostheses which are typically intravascular implants capable of being implanted transluminally and enlarged radially after being introduced percutaneously. Stents may be implanted in a variety of body lumens or vessels such as within the vascular system, urinary tracts, bile ducts, fallopian tubes, coronary vessels, secondary vessels, etc. Stents may be used to reinforce body vessels and to prevent restenosis following angioplasty in the vascular system. They may be self-expanding, expanded by an internal radial force, such as when mounted on a balloon, or a combination of self-expanding and balloon expandable (hybrid expandable).

Stents may be created by methods including cutting or etching a design from a tubular stock, from a flat sheet which is cut or etched and which is subsequently rolled or from one or more interwoven wires or braids.

After stent implantation, it is often desirable as a part of a patient's post-implantation routine to examine the lumen of the stent. Furthermore, it is preferably to use a non-invasive technique such as magnetic resonance imaging (MRI) for such an examination. Although producing excellent imaging results of the body in general, MRI can produce poor quality imaging of stent lumens, a result of the Faraday cage effects caused by the conductive properties of the stent structure and the electromagnetic field of the MRI process.

The art referred to and/or described above is not intended to constitute an admission that any patent, publication or other information referred to herein is "prior art" with respect to this invention. In addition, this section should not be construed to mean that a search has been made or that no other pertinent information as defined in 37 C.F.R. §1.56(a) exists.

All US patents and applications and all other published documents mentioned anywhere in this application are incorporated herein by reference in their entirety.

Without limiting the scope of the invention a brief summary of some of the claimed embodiments of the invention is set forth below. Additional details of the summarized embodiments of the invention and/or additional embodiments of the invention may be found in the Detailed Description of the Invention below.

A brief abstract of the technical disclosure in the specification is provided as well only for the purposes of complying with 37 C.F.R. 1.72. The abstract is not intended to be used for interpreting the scope of the claims.

BRIEF SUMMARY OF THE INVENTION

In some embodiments of the present invention, the stent, with struts and a resonating circuit, is adapted to be implanted into the lumen of a vessel. The resonating circuit includes at least one inductive element and at least one capacitive element. The stent struts in some embodiments are metallic and may be made from such materials as niobium, nitinol, or a biodegradable metal, for example. Or, the stent struts may be formed from a polymer.

In other embodiments, the stent strut includes a notch. In such an embodiment, the resonating circuit may be wound about the notched area in order to reduce the profile of the circuit.

In at least one embodiment, the capacitive element of the resonating circuit can be tubular. In such an embodiment, the tubular-shaped capacitive element can be disposed about a stent strut. Furthermore, the inductive element of the resonating circuit can be shaped as a coil and electrically connected to and wound about the tubular-shaped capacitor. Alternatively, the coil-shaped inductive element can be wound around the stent strut and then the tubular-shaped capacitive element can be fitted over and electrically connected to the coil, like a sleeve.

In some embodiments, the capacitive element of the resonating circuit is ring-shaped and disposed about the stent strut.

In at least one embodiment, the capacitive element of the resonating circuit can be a stub. A stub is a piece of conductive material, designed to produce specific electrical characteristics such as capacitance, that projects outwardly from a structure. In such an embodiment, the inductive element may be a coil wound about the stent strut and the stub electrically connected to and extending from one end of the coil.

Methods of making and using the stents described above can be embodied in various forms. For example, some embodiments provide that an MRI resonating system with a stent implant can be formed to include a resonating circuit wherein the resonating circuit includes at least one capacitive element and at least one inductive element. Further, the resonating circuit is tuned to resonate at substantially the same frequency as an MRI signal. Next, the resonating circuit is disposed about a stent strut. After placing the MRI resonating system within a body lumen, an MRI signal is applied.

In at least one embodiment, a method of making an MRI resonating system with a stent implant may include forming a notched area on a stent strut. In some embodiments, the capacitive element can then be disposed about the notched area on the stent strut. Alternatively, other embodiments provide that the capacitive element is formed about the inductive element.

BRIEF DESCRIPTION OF THE DRAWINGS

A detailed description of the invention is hereafter described with specific reference being made to the drawings.

DETAILED DESCRIPTION OF THE INVENTION

While this invention may be embodied in many different forms, there are described in detail herein specific preferred embodiments of the invention. This description is an exemplification of the principles of the invention and is not intended to limit the invention to the particular embodiments illustrated.

For the purposes of this disclosure, like reference numerals in the figures shall refer to like features unless otherwise indicated.

Depicted in the figures are various aspects of the invention. Elements depicted in one figure may be combined with, and/or substituted for, elements depicted in another figure as desired.

Figure 1:
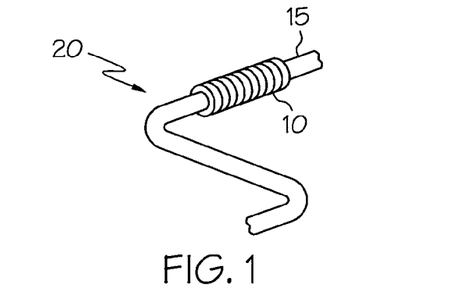
FIG. 1 is a perspective view of a coil wrapped about a stent strut.

FIG. 1 is a perspective view of an embodiment of the present invention. A resonating circuit is achieved by winding a coil 10 about a strut 15 of a stent, a portion shown generally at 20. Although the coil can be wound about around a single strut, the coil must connected to a capacitor and the resonating circuit must encircle the interior of the stent at least once in order to provide amplification of the area. Prior to implantation, the circuit is tuned such that its resonating frequency substantially equals the resonant frequency of the MRI system. Because different elements precess at different frequencies (the Lamor frequency), the resonating frequency of the resonating circuit is dependent upon the element used within the main magnetic field. For example, if hydrogen is used, the resonating circuit must be tuned to 42.58 MHz at 1 Tesla. (Also at 1 Tesla, 17.25 MHz for phosphorous, 11.27 MHz for natrium, and 40.08 for fluorine.) The coil 10 and stent 20 are then implanted within the lumen of a vessel.

In some embodiments of the present invention the struts 15 are metallic, such as niobium, nitinol, or biodegradable metal. In other embodiments, the strut 15 can be made from a polymer. It is also possible to use a biodegradable metal to form the coil 10, allowing both the coil 10 and stent 20 to degrade within the lumen, eliminating the need for a separate medical procedure for their removal.

In some embodiments the stent, the delivery system or other portion of the assembly may include one or more areas, bands, coatings, members, etc. that is (are) detectable by imaging modalities such as X-Ray, MRI, ultrasound, etc. In some embodiments at least a portion of the stent and/or adjacent assembly is at least partially radiopaque.

Figure 2:
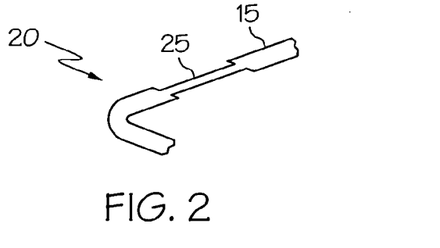
FIG. 2 is a perspective view of a stent strut with a notched region.
Figure 2A:
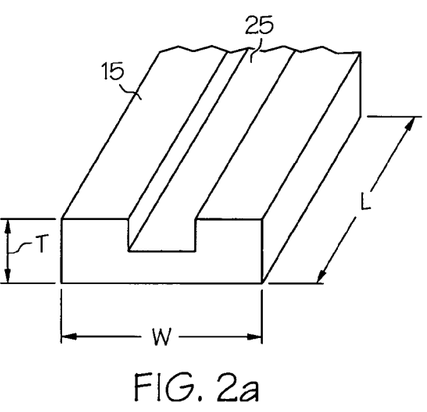
FIG. 2a is a perspective view of a stent strut with a notched region along the length of the strut.
Figure 2B:
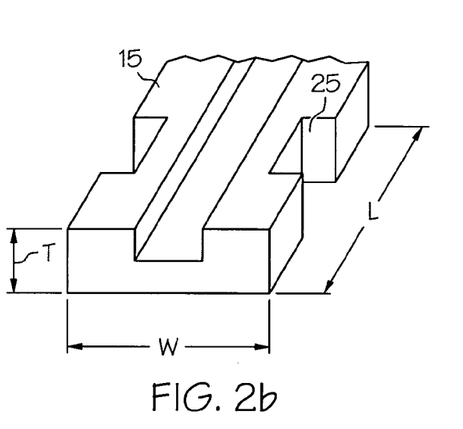
FIG. 2b is a perspective view of the stent strut of FIG. 2a with a notched region along the width.
Figure 2C:
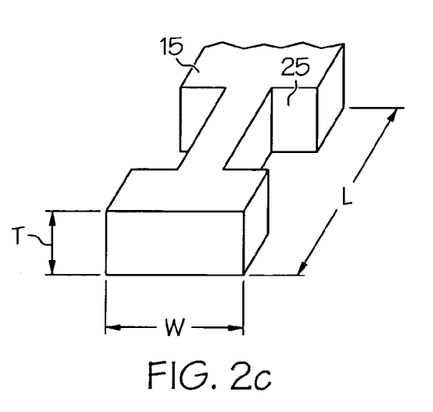
FIG. 2c is a perspective view of a stent strut with a notched region along the width.
Figure 2D:
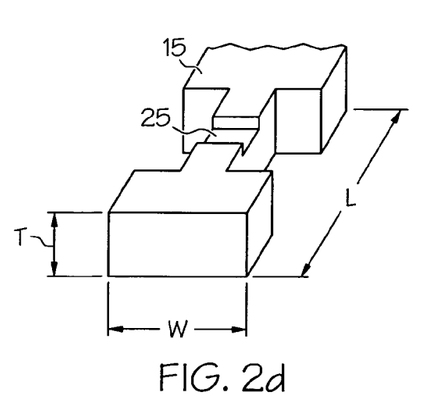
FIG. 2d is a perspective view of the stent strut of FIG. 2c with a notched region along the length.

In at least one embodiment of the present invention, FIG. 2 shows the strut 15 with a notched region 25. If the stent strut is tubular, the strut has a smaller diameter in the notched region 25 than in adjacent regions. If the stent strut is not tubular, than the strut has smaller width and/or smaller thickness in the notched region 25 than in adjacent regions. Thus, the coil (not shown) can be wound about the strut 15 at the notched region 25, thereby minimizing the profile of the circuit and strut combination. Exemplary struts 15 with notched regions 25 are shown in FIGS. 2a-2d.

In some embodiments the at least a portion of the stent is configured to include one or more mechanisms for the delivery of a therapeutic agent. Often the agent will be in the form of a coating or other layer (or layers) of material placed on a surface region of the stent, which is adapted to be released at the site of the stent's implantation or areas adjacent thereto.

A therapeutic agent may be a drug or other pharmaceutical product such as non-genetic agents, genetic agents, cellular material, etc. Some examples of suitable non-genetic therapeutic agents include but are not limited to: anti-thrombogenic agents such as heparin, heparin derivatives, vascular cell growth promoters, growth factor inhibitors, Paclitaxel, etc. Where an agent includes a genetic therapeutic agent, such a genetic agent may include but is not limited to: DNA, RNA and their respective derivatives and/or components; hedgehog proteins, etc. Where a therapeutic agent includes cellular material, the cellular material may include but is not limited to: cells of human origin and/or non-human origin as well as their respective components and/or derivatives thereof. Where the therapeutic agent includes a polymer agent, the polymer agent may be a polystyrene-polyisobutylene-polystyrene triblock copolymer (SIBS), polyethylene oxide, silicone rubber and/or any other suitable substrate.

Figure 3:
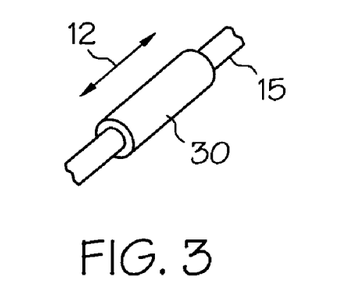
FIG. 3 is a perspective view of a tubular capacitor disposed about the stent strut.
Figure 4:
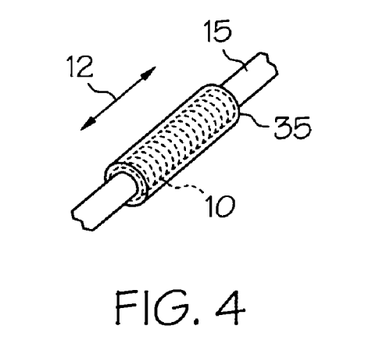
FIG. 4 is a perspective view of a sheath capacitor disposed about a coil wrapped around a strut.
Figure 4A:
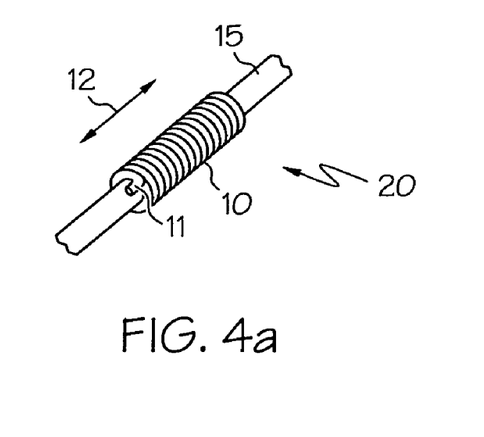
FIG. 4a is a perspective view of a stub capacitor engaged to a coil wrapped around a strut.
Figure 5:
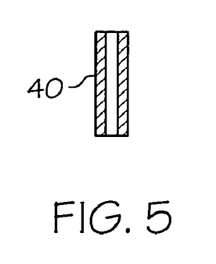
FIG. 5 is a side view of a ring capacitor.
Figure 6:
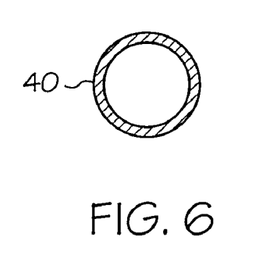
FIG. 6 is a front view of the ring capacitor shown in FIG. 5.

FIG. 3 depicts the capacitive element of the circuit as a substantially tubular device 30 disposed about the strut 15 and extending substantially parallel to the longitudinal axis 12 of strut 15. In this embodiment the inductive coil (not shown) can be wound about and electrically connected to the tubular capacitive element 30. Alternatively, the capacitive element can be a substantially tubular device 35 disposed about the coil 10 that is wound about the stent strut 15, as shown in FIG. 4. Substantially tubular device 35 extends substantially parallel to the longitudinal axis 12 of strut 15. Although the coil and/or capacitor can be wound about around a single strut, the resonating circuit must encircle the stent at least once in order to provide amplification of the interior of the stent. As an alternative to being tubular, the capacitive element can be a stub 111 engaged to the coil 10 that is wound about the stent strut 15, as shown in FIG. 4*a*. A stub is a piece of conductive material, designed to produce specific electrical characteristics such as capacitance, that projects outwardly from a structure. In other embodiments, like in FIG. 5 and FIG. 6 the capacitive element 40 can be ring shaped.

Figure 7:
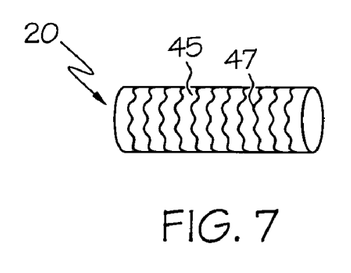
FIG. 7 is a side view of an unexpanded coil disposed about an unexpanded stent.
Figure 8:
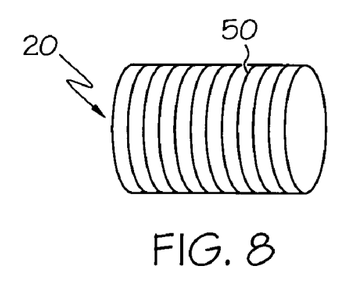
FIG. 8 is a side view of the coil shown in FIG. 7 expanded and disposed about an expanded stent.

Rather than being wound about a strut, another embodiment of the present invention provides that the coil is affixed to the exterior of the stent. FIG. 7 shows an unexpanded stent, shown generally at 20, with a coil 45 affixed to the exterior of the stent 20. When the expandable stent is in an unexpanded state, the coil, also in an unexpanded state and sized for the expanded stent, will have additional material (or "slack"), depicted in FIG. 7 at 45. However, once the stent is expanded, as shown generally at 20 in FIG. 8, the coil 50 is expanded thereby removing the slack 45 of FIG. 7.

There are a number of ways in which the slack 45 of coil 47 in FIG. 7 can be held while the stent is in the unexpanded state. The coil can be designed such that the slack is folded when the coil is not in an expanded state. When expanded the slack of the coil unfolds and expands. In other embodiments, rather than being folded, the slack can take the form of springs. The springs can be fixed to the stent thereby allowing the coil to expand as the stent expands.

Figure 9:
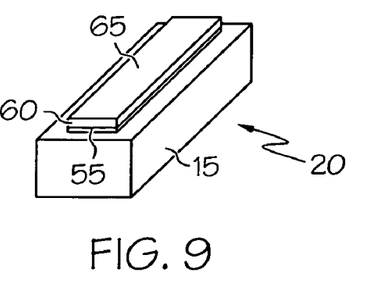
FIG. 9 is a perspective view of a stent strut with a conducting tract.

FIG. 9 depicts an alternate embodiment of the resonating circuit. There, the resonating circuit is formed by conducting tracts 65 attached to the outer surface of strut 15. The conducting tract 65 comprises a conducting layer 60 applied over an insulating layer 55. The insulating layer 55 is applied over the conductive stent material. This design provides the capacitive effects required for a resonating circuit. In some embodiments, the conducing tracts 65 form a continuous helix around the stent. The helix shape of the conducting tracts 65 provides the inductive effects. The conducting tracts 65 can be placed upon the stent by processes similar to photolithography.

Figure 10:
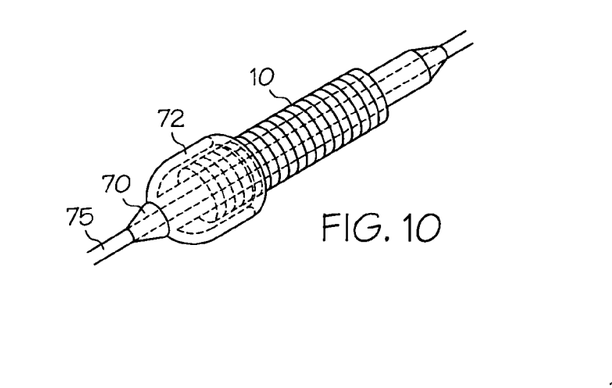
FIG. 10 is a perspective view of a balloon catheter and stent with the balloon folded around the stent.
Figure 11:
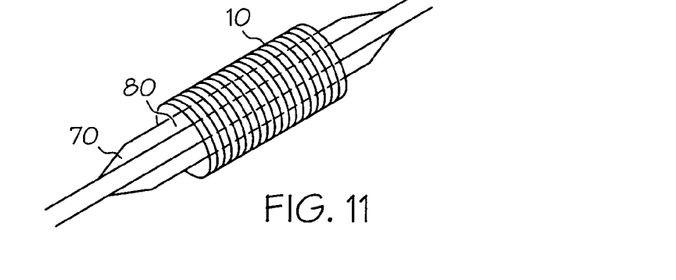
FIG. 11 is a perspective view of balloon catheter and stent with the stent affixed to the balloon with adhesive.

Another embodiment of the present invention, shown in FIG. 10, provides for a resonating circuit 10 to be delivered within a lumen by engagement to the balloon 70 of a balloon catheter 75. FIG. 10 shows one embodiment in which the circuit 10 is engaged to the surface of the balloon 70 by the folds 72 of the balloon 70. That is, the circuit 10 is folded within the balloon 70 such that when the balloon expands, the balloon unfolds, releasing the circuit at the desired location. In other embodiments the circuit 10 can be engaged to the balloon 70 by a biocompatible adhesive 80. The adhesive 80 can be dissolvable, allowing the circuit 10 to be gradually released from the balloon 70. Or, the adhesive 80 can be designed to be brittle, allowing the circuit 10 to be quickly released from the balloon 70. In other words, as the balloon 70 expands, the adhesive engagement points rupture.

Figure 12:
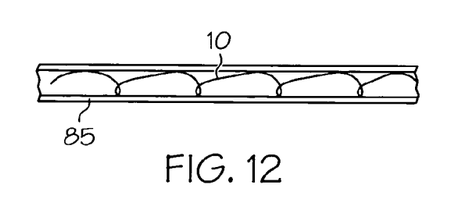
FIG. 12 is a side view of a delivery tube with a coil deformed into a largely linear element.
Figure 13:
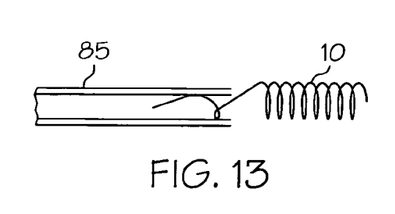
FIG. 13 is a side view of the coil of FIG. 12 being extracted from a delivery tube.
Figure 14:
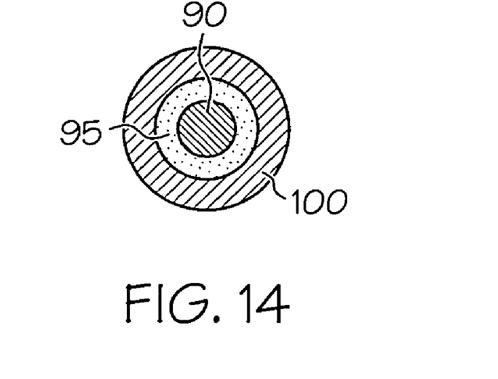
FIG. 14 is a front view of a dielectric and conductor disposed about a wire.
Figure 15:
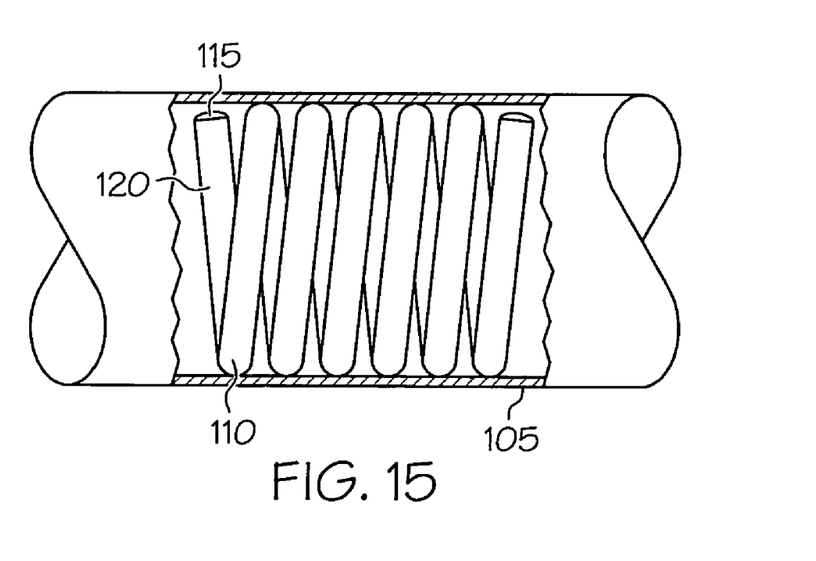
FIG. 15 is a partial cutaway view of a sock with a flexible coil attached therein.

In FIG. 12 the resonating circuit 10, in an alternative construction, can be delivered within the lumen of a vessel through a delivery tube 85. The coil 10 may be formed from a shape-memory material such as nitinol, or from other elastic materials. In this embodiment, the coil 10 is fabricated such that when combined with a capacitive element, the combination resonates at a desired frequency. The coil 10 is then deformed into a substantially linear wire element and inserted into a delivery tube 85. The delivery tube is inserted into the lumen of a vessel. Once placed within the lumen, the linear wire element 10 is extracted from the delivery tube 85, as depicted in FIG. 15. The linear wire element 10, after a delay, will recover its former coil shape. Once the coil has fully recovered, a stent device may be implanted within the coil. FIG. 14 depicts a preferred embodiment of the capacitive element used in conjunction with the coil of FIGS. 12 and 13. The capacitive element is formed by applying a dielectric material 95 onto coil 90 and then applying a conductive layer 100 onto the dielectric material 95.

FIG. 15 depicts such a device formed with a sock 105 and a coil 110. The sock 105 is constructed from a flexible and conformable fabric. The flexible and conformable fabric allows the sock to fit over and maintain engagement with body parts such as ankles, elbows, and knees. The coil 110 is constructed from an elastic tube. The elastic tube is fixed in the form of a coil within the sock 105 so that the tube cannot uncoil into a linear shape. The elastic tube can be formed from such materials as latex or silicone. Furthermore, the elastic tube is filled with a flexible metallic material 120. Once filled, the ends of the elastic tube are capped with caps 115 to prevent the metallic material 120 from leaking. Also, the caps 115 contain electrical contacts, allowing the coil 110 to connect to other electrical elements to form a resonating circuit.

Figure 16:
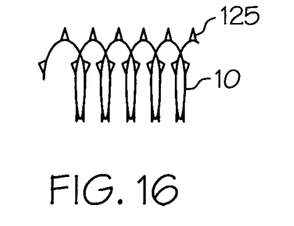
FIG. 16 is a side view of a coil with barbs attached throughout the coil.
Figure 16A:
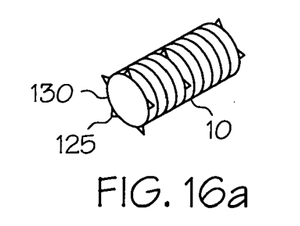
Figure 17:
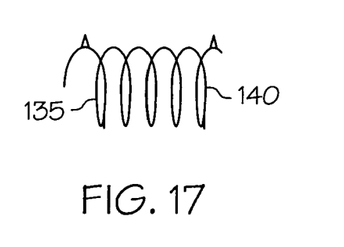
FIG. 17 is a side view of a coil with barbs attached at the ends of the coil.
Figure 18:
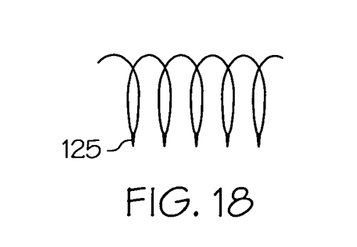
FIG. 18 is a side view of a coil with barbs attached in patterns.

As depicted in FIG. 16, an alternate construction of the present invention provides barbs for securing a resonating circuit within the vessel. In this embodiment, the circuit comprises a coil 10, with barbs 125 located on the exterior 130 of the coil 10, as shown in FIG. 16*a*. The barbs may be hooks or spears with sufficient length and sharpness such that they will embed into the vessel walls. In one embodiment, depicted by FIG. 16, the barbs 125 are located on the entire coil 10. FIG. 17 shows another embodiment where the barbs 125 are located at both the distal end 135 and the proximal end 140 of the coil 10, but not along the rest of coil 10. Or, the barbs may be located at either one of the ends. Alternatively, the barbs 125 may be affixed to the coil 10 in predetermined patterns, as shown in FIG. 18.

In yet another embodiment, the barbs can be oriented on the coil in a direction opposite to the direction of the expanding coil. Thus, once the coil is fully expanded, the barb orientation prevents the coil from unexpanding.

Figure 19:
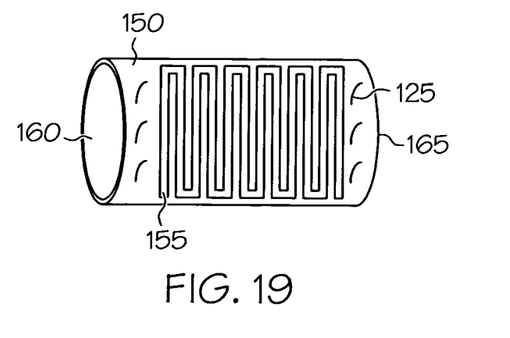
FIG. 19 is a side view of a polymer sheath with a circuit printed thereon with barbs on the ends.

Rather than providing a coil, FIG. 19 illustrates another construction wherein the circuit 155 is printed on a polymer sheath 150. The polymer sheath 150 has a proximal end 160 and a distal end 165 with barbs 125 attached to either end or both, facing outward.

One method of delivering the polymer sheath with circuit includes expanding the polymer sheath with outward facing barbs, engaging the polymer sheath with a balloon catheter, compressing the polymer sheath such that the length of the polymer sheath contracts while the diameter of the polymer sheath expands. Once the polymer sheath has been located within the lumen, the expanded polymer sheath is held in place by the outward facing barbs.

Figure 20:
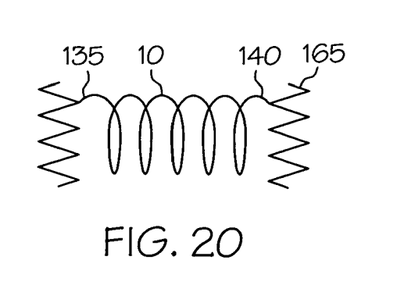
FIG. 20 is a side view of a coil with stent-type structures attached at the ends of the coil.

Another embodiment of securing the resonating circuit 10 within a vessel comprises at least two stent structures 165 engaged to the circuit 10, as shown in FIG. 20. The circuit has proximal end 135 and distal end 140 such that one stent structure 165 is engaged with distal end 140 and one stent structure is engaged to proximal end 135. In one embodiment, the stent structures 165 are formed from a shape memory material.

The above disclosure is intended to be illustrative and not exhaustive. This description will suggest many variations and alternatives to one of ordinary skill in this art. The various elements shown in the individual figures and described above may be combined or modified for combination as desired. All these alternatives and variations are intended to be included within the scope of the claims where the term "comprising" means "including, but not limited to".

Further, the particular features presented in the dependent claims can be combined with each other in other manners within the scope of the invention such that the invention should be recognized as also specifically directed to other embodiments having any other possible combination of the features of the dependent claims. For instance, for purposes of claim publication, any dependent claim which follows should be taken as alternatively written in a multiple dependent form from all prior claims which possess all antecedents referenced in such dependent claim if such multiple dependent format is an accepted format within the jurisdiction (e.g. each claim depending directly from claim 1 should be alternatively taken as depending from all previous claims). In jurisdictions where multiple dependent claim formats are restricted, the following dependent claims should each be also taken as alternatively written in each singly dependent claim format which creates a dependency from a prior antecedent-possessing claim other than the specific claim listed in such dependent claim below.

The invention claimed is:

1. A stent adapted to be implanted into the lumen of a vessel, the stent comprising a plurality of struts defining an interior and a resonating circuit, the resonating circuit comprising at least one inductor and at least one capacitor, the resonating circuit having a resonant frequency substantially equal to the frequency applied by a magnetic resonance imaging system, the at least one inductor in electrical communication with the at least one capacitor, the at least one inductor being a coil wrapped about only one strut of the plurality of struts, the strut having a longitudinal axis, the at least one capacitor being a substantially tubular device disposed about the strut such that the longitudinal axis of the strut extends substantially parallel to a longitudinal axis of the capacitor, wherein the resonating circuit encircles the interior of the stent at least once.

2. The stent of claim 1 wherein the struts are metallic.

3. The stent of claim 2 wherein the struts are niobium.

4. The stent of claim 2 wherein the struts are nitinol.

5. The stent of claim 2 wherein the struts are biodegradable metal.

6. The stent of claim 1 wherein the struts are made from a polymer.

7. The stent of claim 1 wherein at least one strut has a length, a thickness, and a width, along the length the strut defines a notched region, the notched region having a thickness less than the thickness of an adjacent region of the strut.

8. The stent of claim 7 wherein along the width the notched region has a width less than the width of an adjacent region of the strut.

9. The stent of claim 1 wherein at least one strut has a length, a thickness, and a width, along the width the strut defines a notched region, the notched region having a width less than the width of an adjacent region of the strut.

10. The stent of claim 9 wherein along the length the notched region has a thickness less than the thickness of an adjacent region of the strut.

11. The stent of claim 1 wherein the inductor is disposed about the at least one capacitor.

12. The stent of claim 1 wherein the capacitor is disposed about the at least one inductor.

13. The stent of claim 1 wherein the at least one capacitor is ring-shaped.

14. The stent of claim 1 wherein the at least one capacitor is a stub.

15. A method of making and using MRI resonating system with a stent implant comprising the steps of:
    providing a resonating circuit, the circuit comprising at least one inductive element and at least one capacitive element, the circuit having a resonant frequency substantially equal to the frequency applied by a magnetic resonance imaging system;
    wrapping the inductive element about only one strut of a stent, the stent having an interior, wherein the resonating circuit encircles the interior of the stent at least once;
    disposing the capacitive element about the stent strut, wherein the capacitive element is a substantially tubular device;
    placing the MRI resonating system within a body lumen; and
    applying an MRI signal.

16. The method of claim 15 further comprising the step of forming a notched region on the strut.

17. The method of claim 16 wherein the inductive element is disposed about the notched region of the strut.

18. The method of claim 15 wherein the capacitive element is disposed about the stent strut before the inductive element is wrapped about the strut.

19. The method of claim 15 wherein the capacitive element is disposed about the inductive element.

20. A stent adapted to be implanted into the lumen of a vessel, the stent comprising struts defining an interior and a resonating circuit, the resonating circuit comprising at least one inductor and at least one capacitor, the resonating circuit having a resonant frequency substantially equal to the frequency applied by a magnetic resonance imaging system, the at least one inductor in electric communication with the at least one capacitor, the at least one inductor being a coil, at least one strut having a length, a thickness, and a width, along the width the strut defines a notched region, the notched region having a width less than the width of an adjacent region of the at least one strut, the coil being wound about the notched region of the strut, the capacitor being a tubular member disposed about the strut, wherein the resonating circuit encircles the interior of the stent at least once.

* * * * *